(12) United States Patent
Yoshimoto et al.

(10) Patent No.: US 7,795,452 B2
(45) Date of Patent: Sep. 14, 2010

(54) CHARGE-TRANSPORTING ORGANIC MATERIAL CONTAINING COMPOUND HAVING 1,4-DITHIIN RING

(75) Inventors: Takuji Yoshimoto, Funabashi (JP); Go Ono, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 775 days.

(21) Appl. No.: 10/577,438

(22) PCT Filed: Oct. 29, 2004

(86) PCT No.: PCT/JP2004/016095

§ 371 (c)(1), (2), (4) Date: Apr. 27, 2006

(87) PCT Pub. No.: WO2005/043962

PCT Pub. Date: May 12, 2005

(65) Prior Publication Data

US 2007/0043222 A1  Feb. 22, 2007

(30) Foreign Application Priority Data

Oct. 31, 2003  (JP) .............................. 2003-371782

(51) Int. Cl.
*C07D 409/14* (2006.01)
(52) U.S. Cl. ...................................................... 549/14
(58) Field of Classification Search .................... 549/14
See application file for complete search history.

(56) References Cited

U.S. PATENT DOCUMENTS 4,319,033 A  3/1982  Tsai et al.

FOREIGN PATENT DOCUMENTS

| JP | 56-049304 A | 5/1981 |
| JP | 57-140782 A | 8/1982 |
| JP | 61-152677 A | 7/1986 |
| JP | 2002-151272 A | 5/2002 |

OTHER PUBLICATIONS

Juzo Nakayama et al., Preparation of α-Quinine and α-Septithiophenes and Their Positional Isomers, Heterocycles, 1987, 939-943, 26-4.

S. A. Van Slyke, Organic electroluminescent devices with improved stability, Applied Physics Letters, Oct. 7, 1996, 2160-2162, 69-15, US.

G. Gustafsson et al., Flexible light-emitting diodes made from soluble conducting polymers, Nature, Jun. 11, 1992, 477-479, 357, UK.

Y. Yang et al., Polyaniline as a transparent electrode for polymer light-emitting diodes: Lower operating voltage and higher efficiency, Applied Physics Letters, Mar. 7, 1994, 1245-1247, 64-10, US.

Jayesh Bharathan et al., Polymer electroluminescent devices processed by inkjet printing: I. Polymer light-emitting logo, Applied Physics Letters, May 25, 1998, 2660-2662, 72-21, US.

Takeo Wakimoto et al., Organic EL Cells Using Alkaline Metal Compunds as Elecron Injection Materials, IEEE Transactions on Electron Devices, Aug. 1997, 1245-1248, 44-8, US.

L.S. Hung et al., Enhanced electron injection in organic electroluminescence devices using an Al/LiF electrode, Applied Physics Letters, Jan. 13, 1997, 152-154, 70-2, US.

Chimed Ganzorig et al., A Lithium Carboxylate Ultrathin Film on an Aluminum Cathode for Enhanced Electron Injection in Organic Electroluminescent Devices, Japanese Journal of Applied Physics, Nov. 15, 1999, 1348-1350, 38-11.

William E. Parham et al., Heterocyclic Vinyl Ethers, Journal of the American Chemical Society, Apr. 5, 1953, 1647-1651, 75.

Juzo Nakayama et al., General Synthesis of 1,4-Dithiins from Diketo Sulfides, Heterocycles, 1984, 1527-1530, 22-7.

*Primary Examiner*—Taofiq A Solola
(74) *Attorney, Agent, or Firm*—Birch, Stewart, Kolasch & Birch, LLP

(57) ABSTRACT

A charge-transporting organic material containing a compound with a 1,4-dithiin ring, which is represented by the following formula (1), is described.

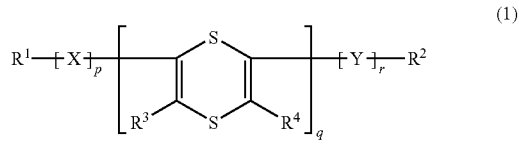

(1)

When using a thin film made of such an organic material in a low-molecular-weight organic EL (OLED) element and a polymer organic EL (PLED) element, EL element characteristics such as low drive voltage and high luminous efficiency can be improved. In addition, a charge-transporting varnish containing the compound with a 1,4-dithiin ring represented by the above formula (1) has good processing properties, and a thin film obtained therefrom has high charge-transporting characteristics and thus is effective for application to protective films for capacitor electrodes, antistatic films, solar cells or fuel cells.

14 Claims, 2 Drawing Sheets

CHARGE-TRANSPORTING ORGANIC MATERIAL CONTAINING COMPOUND HAVING 1,4-DITHIIN RING

TECHNICAL FIELD

This invention relates to a charge-transporting organic material containing a compound with a 1,4-dithiin ring, and also to a charge-transporting thin film and an organic electroluminescent (hereinafter abbreviated as EL) element, both using the same.

BACKGROUND ART

Organic EL elements are broadly classified into low-molecular-weight organic EL (hereinafter abbreviated as OLED) elements and polymer organic EL (hereinafter abbreviated as PLED) elements. With the OLED element, it has been found that a copper phthalocyanine (CUPC) layer is provided as a hole injection layer thereby enabling one to improve initial characteristics, e.g. a lowering of drive voltage, an improved luminous efficiency and the like, and also to improve a life characteristic (see, for example, Non-patent Document 1).

On the other hand, with the PLED element, it has been found that when using polyaniline-type materials (see, for example, Non-patent Documents 2 and 3) and polythiophene-type materials (see, for example, Non-patent Document 4) as a hole transport layer (buffer layer), similar effects are obtained.

It has also been found that when using, at a cathode side, metal oxides (see, for example, Non-patent Document 5), metal halides (see, for example, Non-patent Document 6), and metal complexes (see, for example, Non-patent Document 7) as an electron injection layer, initial characteristics can be improved. These charge injection layer and buffer layer have now been in general use.

In recent years, a charge transporting vanish in the form of an organic solution using a low-molecular-weight oligoaniline-type material has been discovered, and it has now been appreciated that excellent EL element characteristics are shown when inserting a hole injection layer obtained by use of the varnish into an EL element (see, for example, Patent Document 1).

A vacuum deposition material has been widely used as a hole injection material for OLED elements. The problems involved in the vacuum deposition material reside in that they are in an amorphous solid and should have diverse characteristic properties such as sublimability, high heat resistance, and appropriate ionization potential (hereinafter abbreviated as $I_p$), and thus, limitation is place on the type of material.

Since a vacuum deposition material is difficult to dope, high charge transportability is unlikely to be shown with the film obtained by a vacuum deposition method, with a difficulty in increasing a charge injection efficiency. Moreover, CuPC used as a hole injection material is very irregular in shape and is thus disadvantageous in that when the material is incorporated into other organic layers of an EL element in small amounts, characteristics lower.

Although conjugated oligomers or polymers are materials having high charge transportability, most of them are so low in solubility that it is difficult to prepare a varnish and thus, film formation thereof is possible only by a vacuum deposition method. Particularly, in non-substituted thiophene oligomers, molecules each combined more than four subunits are mostly insoluble in every solvents.

For use as hole transport materials of PLED elements, they should have demand characteristics such as high charge transportability, insolubility in solvents for light-emitting polymer such as toluene, appropriate $I_p$ and the like. Polyaniline-type materials and polythiophene-type materials, which have been frequently employed at present, have the problems in that they contain, as a solvent, water that has the possibility of facilitating element degradation, they are so low in solubility that limitation is placed on the selection of solvent, material coagulation is liable to occur, and limitation is placed on the manner of uniform film formation.

On the other hand, synthesis of compounds having a 1,4-dithiin ring have been reported in document (e.g. Non-patent Documents 8 to 10). The processes of preparing compounds having a 1,4-dithiin ring that are set out in Non-patent Documents 9 and 10 are not only disadvantageous in that those processes have a number of steps and are difficult to mass-produce, but also low in yield, thus improvements thereof being necessary.

Non-Patent Document 1:
Applied Physics Letters, U.S.A., 1996, Vol. 69. pp. 2160-2162
Non-Patent Document 2:
Nature, Britain, 1992, Vol. 357, pp. 477-479
Non-Patent Document 3:
Applied Physics Letters, U.S.A., 1994, Vol. 64, pp. 1245-1247
Non-Patent Document 4:
Applied Physics Letters, U.S.A., 1998, Vol. 72, pp. 2660-2662
Non-Patent Document 5:
IEEE Transactions on Electron Devices, U.S.A., 1997, Vol. 44, pp. 1245-1248
Non-Patent Document 6:
Applied Physics Letters, U.S.A., 1997, Vol. 70, pp. 152-154
Non-Patent Document 7:
Japanese Journal of Applied Physics, 1999, Vol. 38, pp. 1348-1350
Non-Patent Document 8:
Journal of American Chemical Society, 1953, Vol. 75, pp. 1647-1651
Non-Patent Document 9:
Heterocycles, 1984, Vol. 22, p. 1527
Non-Patent Document 10:
Heterocycles, 1987, Vol. 26, pp. 939-942
Patent Document 1:
Japanese Patent Laid-open No. 2002-151272

DISCLOSURE OF INVENTION

Problems to be Solved by the Invention

Under these circumstances, the invention has for its object the provision of a charge transporting organic material containing a compound having a 1,4-dithiin ring and ensuring excellent EL element characteristics, i.e. low drive voltage and high luminous efficiency, especially when used in OLED elements and PLED elements and a charge transporting varnish, and also to a charge transporting thin film and an organic electroluminescent element using the same.

Means for Solving the Problems

We made intensive studies in order to achieve the above object and, as a result, found that a compound having a 1,4-dithiin ring is one that is soluble in an organic solvent such as N,N-dimethylformamide (hereinafter abbreviated as DMF), and is able to develop charge transportability when used in combination with an electron accepting dopant substance or hole accepting dopant and enables one to attain low voltage drive and an improved luminous efficiency when used as a charge transporting thin film such as a hole injection layer of an OLED element, thereby accomplishing the invention.

More particularly, the invention provides the following inventions [1] to [11].

[1] A charge transport organic material that contains a compound having a 1,4-dithiin ring and represented by the general formula (1)

[Chemical Formula 1]

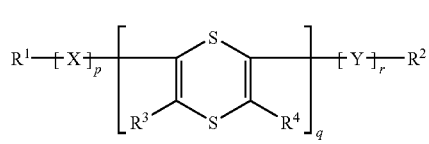

(1)

(wherein $R^1$, $R^2$, $R^3$ and $R^4$ independently represent hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group, an organooxy group, an organoamino group, an organosilyl group, an organothio group, an acyl group or a sulfone group, X and Y independently represent at least one member of substituted or unsubstituted, divalent conjugated units selected from aniline, thiophene, furan, pyrrole, ethynylene, vinylene, phenylene, naphthalene, anthracene, imidazole, oxazole, oxadiazole, quinoline, quinoxaline, pyridine, pyrimidine, pyrazine, phenylenevinylene, fluorene, carbazole, triarylamine, metal or metal-free phthalocyanine, and metal or metal-free porphyrin, two sulfur atoms contained in the dithiin ring may independently be in the form of an SO group or an $SO_2$ group, and p, q and r independently represent 0 or an integer of 1 or over provided that p+q+r≦20 is satisfied).

[2] The charge transport organic material of [1], further comprising an electron accepting dopant substance or a hole accepting dopant substance.

[3] The charge transport organic material of [1] or [2] wherein p, q and r in the general formula (1) satisfies that 3≦p+q+r≦10.

[4] A charge transport varnish comprising a charge transport organic material of any one of [1] to [3] and a solvent.

[5] A charge transport thin film prepared by use of the charge transport varnish of [4].

[6] An organic electroluminescent element comprising the charge transport thin film of [5].

[7] A method for preparing a compound having a 1,4-dithiin ring and represented by the formula (1) indicated hereinbelow, characterized by comprising:

the first step of reacting, in the presence of an acid catalyst, a compound of the formula (2)

[Chemical Formula 2]

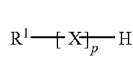

(2)

(wherein $R^1$ hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group or an organooxy group, X represents at least one member of substituted or unsubstituted, divalent conjugated units selected from aniline, thiophene, furan, pyrrole, ethynylene, vinylene, phenylene, naphthalene, anthracene, imidazole, oxazole, oxadiazole, quinoline, quinoxaline, pyridine, pyrimidine, pyrazine, phenylenevinylene, fluorene, carbazole, triarylamine, metal or metal-free phthalocyanine, and metal or metal-free porphyrin, and p is an 0 or an integer of 1 or over), or a compound of the formula (3)

[Chemical Formula 3]

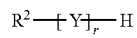

(3)

(wherein $R^2$ represents hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group or an organooxy group, Y represents at least one member of substituted or unsubstituted, divalent conjugated units selected from aniline, thiophene, furan, pyrrole, ethynylene, vinylene, phenylene, naphthalene, anthracene, imidazole, oxazole, oxadiazole, quinoline, quinoxaline, pyridine, pyrimidine, pyrazine, phenylenevinylene, fluorene, carbazole, triarylamine, metal or metal-free phthalocyanine, and metal or metal-free porphyrin, and r is 0 or an integer of 1 or over), and an acid halide represented by the formula (4)

[Chemical Formula 4]

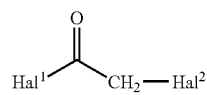

(4)

(wherein Hal represents a halogen atom), thereby preparing an acyl compound represented by the formula (5)

[Chemical Formula 5]

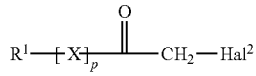

(5)

(wherein $R^1$, X, p and Hal, respectively, have the same meanings as defined above), or the formula (6)

[Chemical Formula 6]

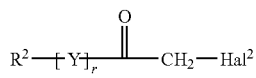

(6)

(wherein $R^2$, Y, r and Hal, respectively, have the same meanings as defined above);

the second step of subsequently reacting the acyl compound represented by the formula (5), the acyl compound represented by the formula (6) and an alkali metal sulfide to prepare a sulfide represented by the formula (7)

[Chemical Formula 7]

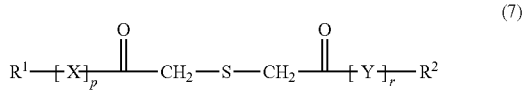

(7)

(wherein $R^1$, $R^2$, X, Y, p and r, respectively, have the same meanings as defined above); and the third step of acting a thiocarbonyl reagent on the sulfide represented by the formula (7) for ring-closure, thereby preparing the compound of the formula (1) having a 1,4-dithiin ring

[Chemical Formula 8]

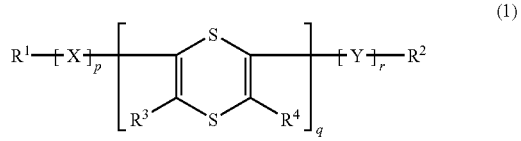

(1)

(wherein $R^1$, $R^2$, X, Y, p and r, respectively, have the same meanings as defined above, $R^3$ and $R^4$ independently represent hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group or an organooxy group, an organoamino group, an organosilyl group, an organothio group, an acyl group or a sulfone group, two sulfur atoms contained in the dithim ring may independently be in the form of an SO group or an $SO_2$ group, and q is 0 or an integer of 1 or over provided that $p+q+r \leq 20$ is satisfied.

[8] A method for preparing an acyl compound of the formula (5) or (6) indicated hereinbelow, characterized by comprising:

reacting, in the presence of an acid catalyst, a compound of the formula (2)

[Chemical Formula 9]

(2)

(wherein $R^1$ represents hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group or an organooxy group, X represents at least one member of substituted or unsubstituted, divalent conjugated units selected from aniline, thiophene, furan, pyrrole, ethynylene, vinylene, phenylene, naphthalene, anthracene, imidazole, oxazole, oxadiazole, quinoline, quinoxaline, pyridine, pyrimidine, pyrazine, phenylenevinylene, fluorene, carbazole, triarylamine, metal or metal-free phthalocyanine, and metal or metal-free porphyrin, and p is 0 or an integer of 1 or over) or the formula (3)

[Chemical Formula 10]

(3)

(wherein $R^2$ represents hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group or an organooxy group, Y represents at least one member of substituted or unsubstituted, divalent conjugated units selected from aniline, thiophene, furan, pyrrole, ethynylene, vinylene, phenylene, naphthalene, anthracene, imidazole, oxazole, oxadiazole, quinoline, quinoxaline, pyrazine, pyrimidine, pyridine, phenylenevinylene, fluorene, carbazole, triarylamine, metal or metal-free phthalocyanine, and metal or metal-free porphyrin, and r is 0 or an integer of 1 or over), and an acid halide of the formula (4)

[Chemical Formula 11]

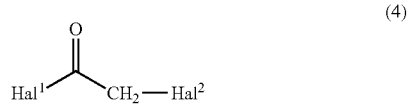

(4)

(wherein Hal represents a halogen atom), thereby preparing the acyl compound of either the formula (5)

[Chemical Formula 12]

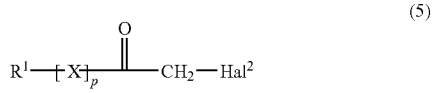

(5)

(wherein $R^1$, X, p and Hal, respectively, have the same meanings as defined above), or the formula (6)

[Chemical Formula 13]

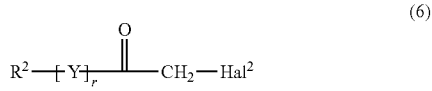

(6)

(wherein $R^2$, X, r and Hal, respectively, have the same meanings as defined above).

[9] The method of [8] for preparing an acyl compound, wherein said acid catalyst is made of ethyl aluminium dichloride or diethyl aluminium, chloride.

[10] A method for preparing a sulfide represented by the formula (7) indicated below, characterized by reacting the acyl compound represented by the formula (5), the acyl compound represented by the formula (6), both obtained in [8] or [9], and an alkali metal sulfide

[Chemical Formula 14]

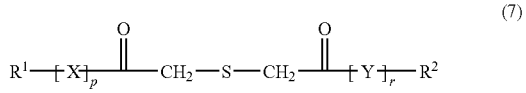

(wherein $R^1$, $R^2$, X, Y, p and r, respectively, have the same meanings as defined above).

[11] A method for preparing a compound having a 1,4-dithiin ring and represented by the formula (1) indicated hereinbelow, characterized by reacting a thiocarbonylizing reagent on the sulfide obtained in [10] and represented by the formula (7)

[Chemical Formula 15]

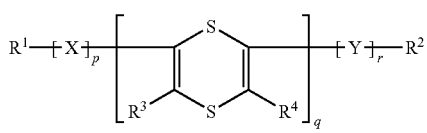

(wherein $R^1$, $R^2$, X, Y, p and r, respectively, have the same meanings as defined above, and $R^3$ and $R^4$ independently represent hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group, an organooxy group, an organoamino group, an organosilyl group, an organothio group, an acyl group or a sulfone group, two sulfur atoms contained in the dithiin ring may independently be in the form of an SO group or an $SO_2$ group, and q is 0 or an integer of 1 or over provided that $p+q+r \leq 20$ is satisfied.

Effects of the Invention

A charge transporting thin film obtained from a charge transport varnish containing a charge transport organic material according to the invention is formed on the surface of an electrode. When this film is used as a charge injection layer of an organic EL element, a charge injection barrier between the electrode and the organic layer lowers, thereby ensuring a lowering of drive voltage and an improved luminous efficiency.

This charge transporting varnish can be employed by use of an organic solvent alone, unlike a conventionally employed aqueous charge transporting varnish, so that not only incorporation of moisture that invites degradation of the element is prevented, but also film formation by a wet process is easily feasible, thus without resorting to a vacuum deposition method for film formation. Accordingly, it is possible to apply, to an organic EL element, a group of conjugated oligomers that are poor in sublimability and heat resistance. It will be noted that the compound having a dithiin ring contained in the charge transporting organic material of the invention can be readily doped with a charge accepting dopant substance.

The charge transporting varnish of the invention has good processability, and the film obtained therefrom has high charge transporting characteristics, thus being effective for application to protective films for capacitor electrodes, antistatic films, solar cells and fuel cells.

BEST MODE FOR CARRYING OUT THE INVENTION

Figure 1:
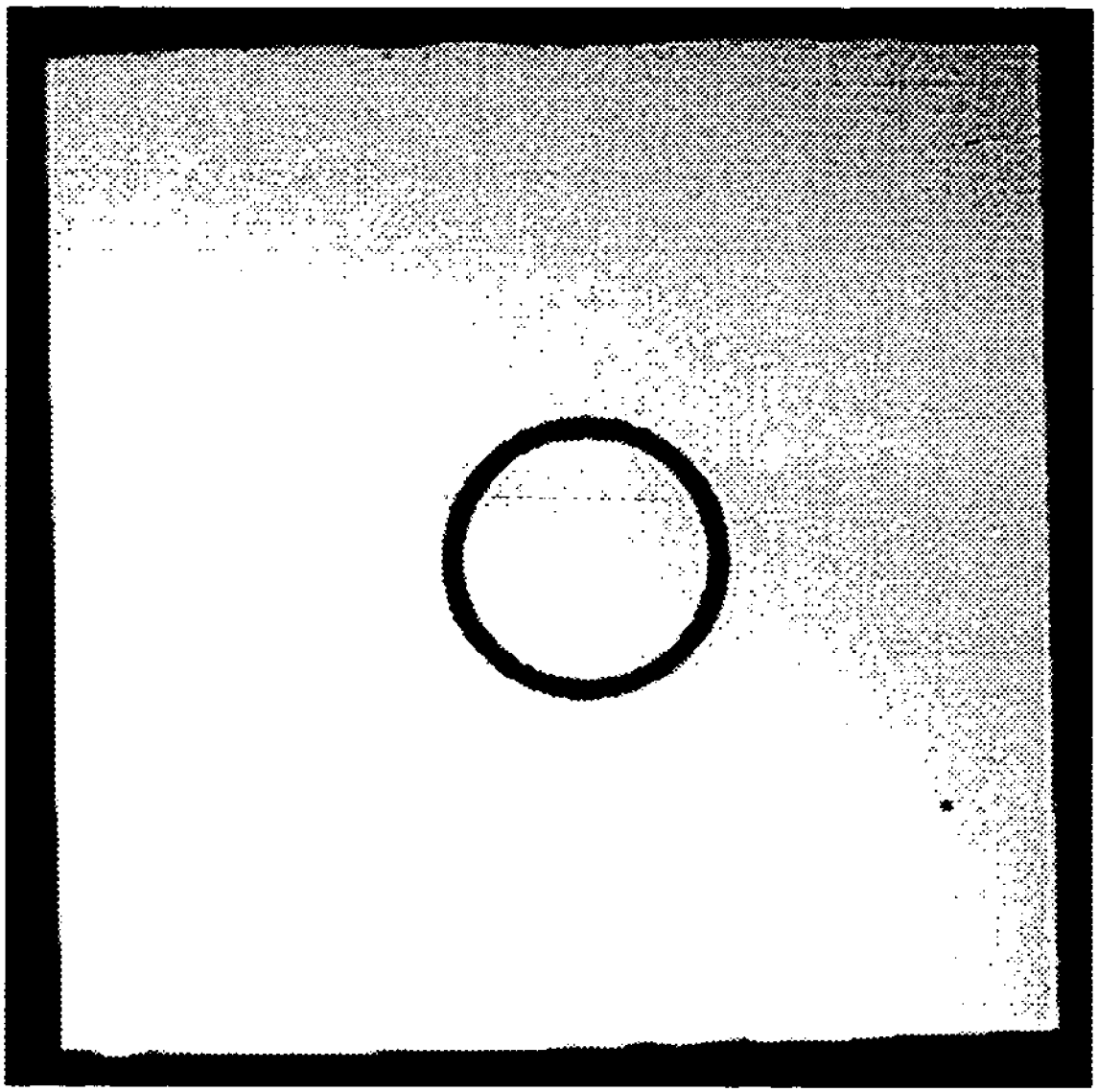
FIG. 1 is a view showing a photograph of a luminous face of an OLED element obtained in Example 7.

The invention is described in more detail.

The charge transporting organic material (charge transporting varnish) of the invention is one which contains a charge transporting substance that plays a main role of charge transport mechanism.

For charge transport organic materials, combinations of charge transporting substances and charge accepting dopants capable of improving charge transportability of the charge transporting substance may also be used.

For a charge transporting varnish, mention is made of a varnish containing a combination of two types of charge transporting substance and solvent, or a combination of three types of charge transporting substance, charge accepting dopant substance and solvent, in which the substances are completely dissolved or uniformly dispersed in solvent.

The charge transportability used herein has the same meaning as conductivity and means any of hole transportability, electron transportability and charge transportability of both holes and electrons. The charge transporting varnish may be one that has charge transportability in itself or may be one wherein a solid film obtained form the varnish has charge transportability.

The charge transporting substance contained in the charge transporting organic material (charge transporting varnish) is a compound of the following formula (1) having a 1,4-dithiin ring

[Chemical Formula 16]

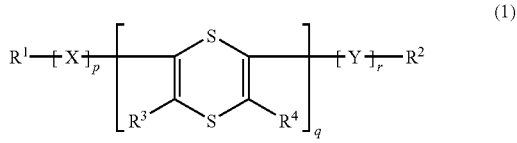

(wherein $R^1$, $R^2$, $R^3$ and $R^4$ independently represent hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group, an organooxy group, an organoamino group, an organosilyl group, an organothio group, an acyl group or a sulfone group, X and Y independently represent at least one member of substituted or unsubstituted, divalent conjugated units selected from aniline, thiophene, furan, pyrrole, ethynylene, vinylene, phenylene, naphthalene, anthracene, imidazole, oxazole, oxadiazole, quinoline, quinoxaline, pyridine, pyrimidine, pyrazine, phenylenevinylene, fluorene, carbazole, triarylamine, metal or metal-free phthalocyanine, and metal or metal-free porphyrin, two sulfur atoms contained in the dithiin ring may independently be in the form of an SO group or an $SO_2$ group, and p, q and r independently represent 0 or an integer of 1 or over provided that $p+q+r \leq 20$ is satisfied).

In the formula, p, q and r should preferably be such that p+q+r≦20, more preferably p+q+r≦10, from the standpoint that solubility of the compound is increased. In view of the development of high charge transportability, 3≦p+q+r is preferred and 5≦p+q+r is more preferred.

The conjugated units represented by X and Y in the formula may, respectively, be an atom, an aromatic ring or a conjugated group capable of transporting charges and are not limited to any specific ones. Preferably, mention is made of substituted or unsubstituted, divalent aniline, thiophene, furan, pyrrole, ethynylene, vinylene, phenylene, naphthalene, anthracene, imidazole, oxazole, oxadiazole, quinoline, quinoxaline, pyridine, pyrimidine, pyrazine, phenylenevinylene, fluorene, carbazole, triarylamine, metal or metal-free phthalocyanine, and metal or metal-free porphyrin. Preferably, thiophene, furan, pyrrole, phenylene, triarylamine and the like are mentioned.

Specific examples of the substituents, respectively, include a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group, an organooxy group, an organoamino group, an organosilyl group, an organothio group, an acyl group and a sulfone group, which may be further substituted with any of these functional groups.

Specific examples of the monovalent hydrocarbon group include alkyl groups such as a methyl group, an ethyl group, a propyl group, a butyl group, a t-butyl group, a hexyl group, an octyl group, a decyl group and the like, cycloalkyl groups such as a cyclopentyl group, a cyclohexyl group and the like, bicycloalkyl groups such as a bicyclohexyl group and the like, alkenyl groups such as a vinyl group, a 1-propenyl group, a 2-propenyl group, an isopropenyl group, a 1-methyl-2-propenyl group, a 1 or 2 or 3-butenyl group, a hexenyl group and the like, aryl groups such as a phenyl group, a xylyl group, a tolyl group, a biphenyl group, a naphthyl group and the like, aralkyl groups such as a benzyl group, a phenylethyl group, a phenylcyclohexyl group and the like, and those groups wherein part or all of hydrogen atoms of these monovalent hydrocarbon groups may be replaced by a halogen atom, a hydroxyl group, an alkoxy group and the like.

For the organooxy group, mention is made of an alkoxy group, an alkenyloxy group, an aryloxy group and the like, in which the alkyl group, alkenyl group and aryl group are those mentioned above.

For the organoamino group, mention is made of alkylamino groups such as a methylamino group, an ethylamino group, a propylamino group, a butylamino group, a pentylamino group, a hexylamino group, a heptylamino group, an octylamino group, a nonylamino group, a decylamino group, a laurylamino group and the like, dialkylamino groups such as a dimethylamino group, a diethylamino group, a dipropylamino group, a dibutylamino group, a dipentylamino group, a dihexylamino group, a diheptylamino group, dioctylamino group, a dinonylamino group, a didecylamino group and the like, a cyclohexylamino group, a morpholino group and the like.

For the organosilyl group, mention is made of a trimethylsilyl group, a triethylsilyl group, a tripropylsilyl group, a tributylsilyl group, a tripentylsilyl group, a trihexylsilyl group, a pentyldimethylsilyl group, a hexyldimethylsilyl group, an octyldimethylsilyl group, a decyldimethylsilyl group and the like.

For the organothio group, mention is made of alkylthio groups such as a methylthio group, an ethylthio group, a propylthio group, a butylthio group, a pentylthio group, a hexylthio group, a heptylthio group, an octylthio group, a nonylthio group, a decylthio group, a laurylthio group and the like.

For the acyl group, mention is made of a formyl group, an acetyl group, a propionyl group, a butyryl group, an isobutyryl group, a valeryl group, an isovaleryl group, a benzoyl group and the like.

Although no limitation is placed on the number of carbon atoms in the monovalent hydrocarbon group, organooxy group, organoamino group, organosilyl group, organothio group, acyl group and the like, the number of carbon atoms generally ranges 1 to 20, preferably 1 to 8.

For a preferred substituent group, mention is made of fluorine, a sulfonic acid group, and a substituted or unsubstituted organooxy group, alkyl group and organosilyl group.

The conjugated chain formed by connecting conjugated units may contain a cyclic moiety. It will be noted that the cyclic moiety should preferably have no substituent group from the standpoint of the achivement of high charge transportability. Specific examples of the compound represented by the afore-indicated formula (1) include those mentioned hereinbelow.

[Chemical Formula 17]

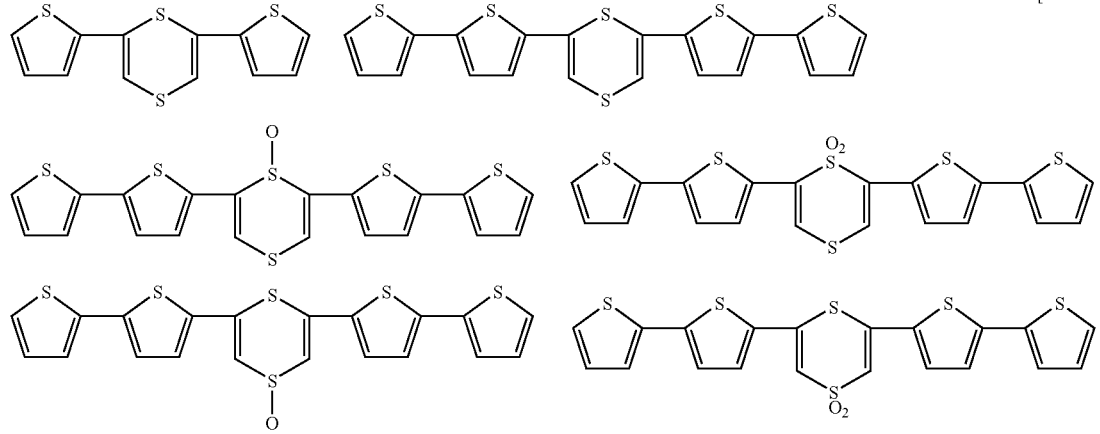

-continued
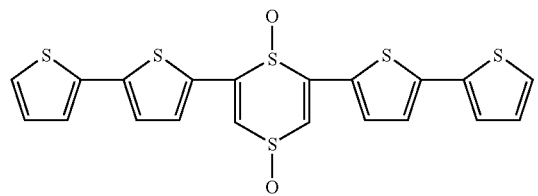 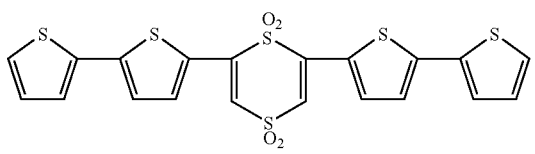
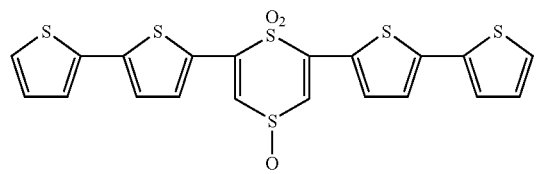 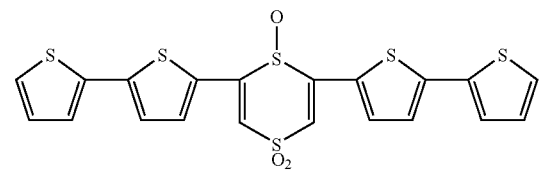
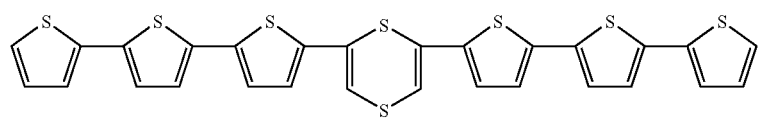
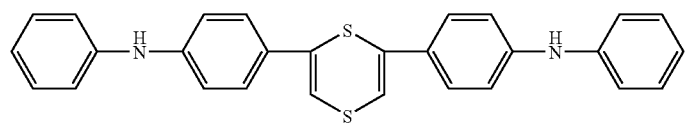
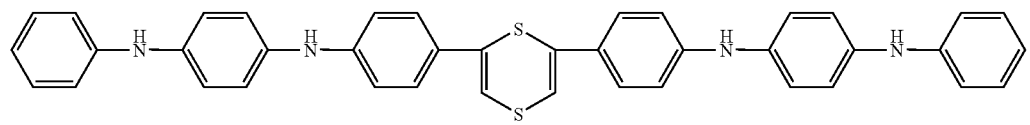
[Chemical Formula 18]
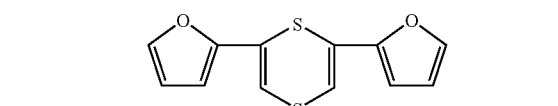 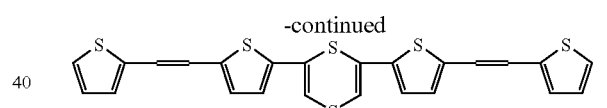
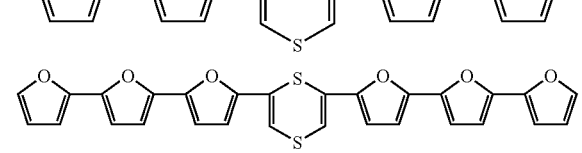 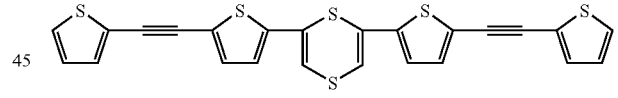
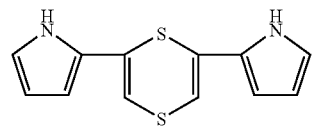 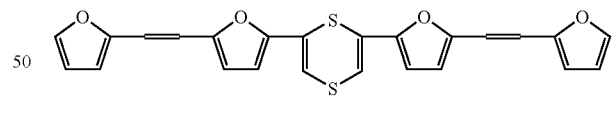
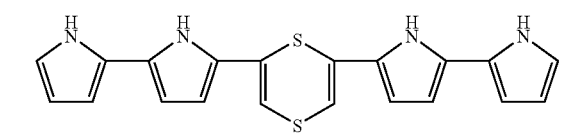 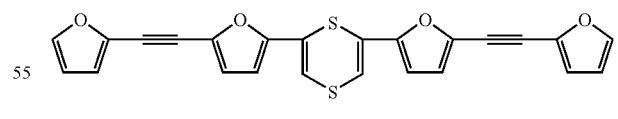
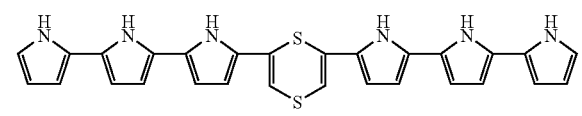 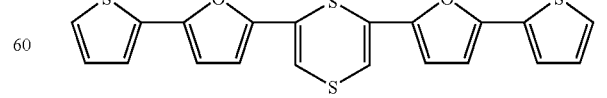
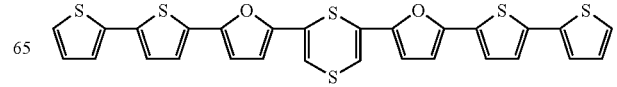

[Chemical Formula 19]
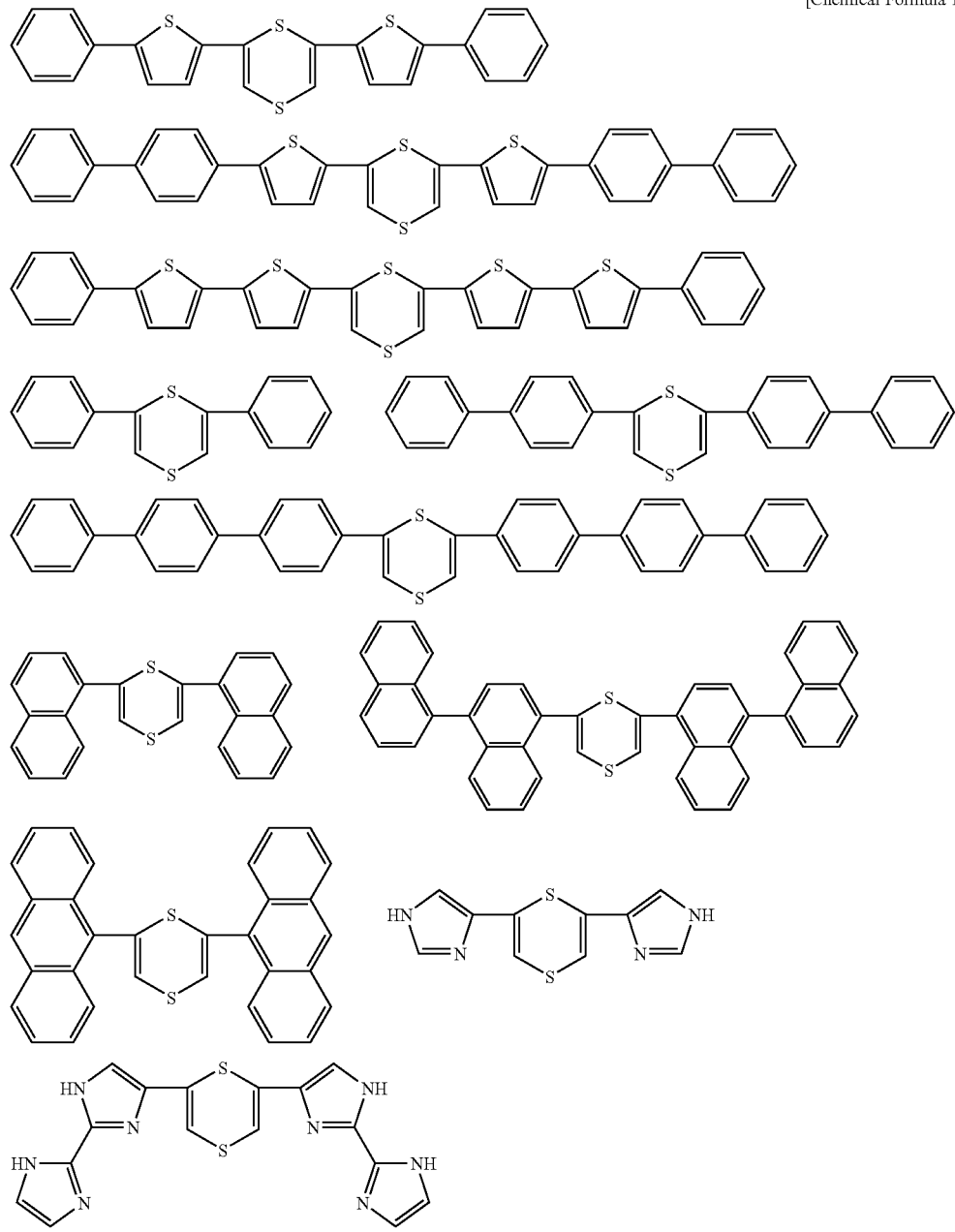
[Chemical Formula 20]
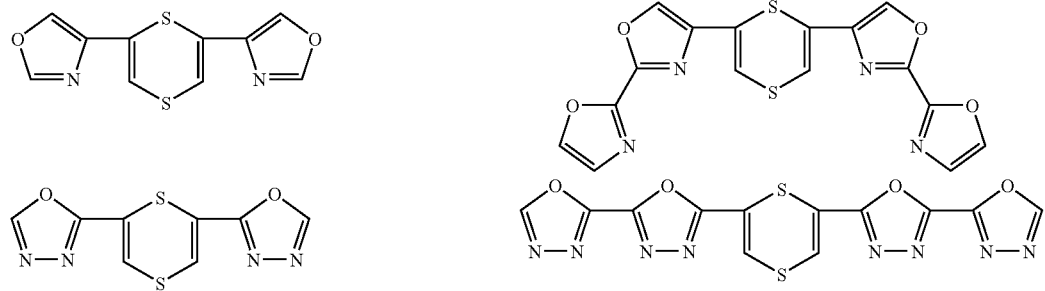

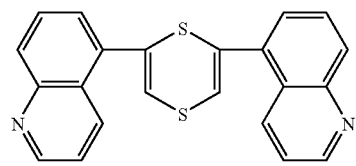
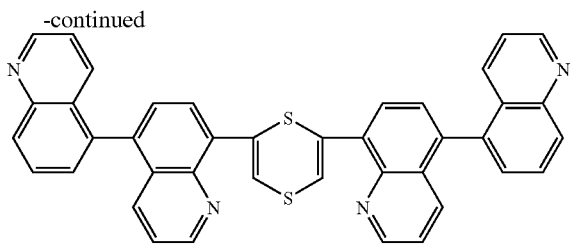
-continued
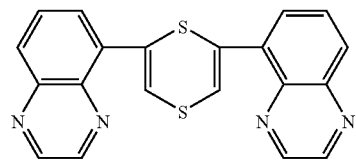
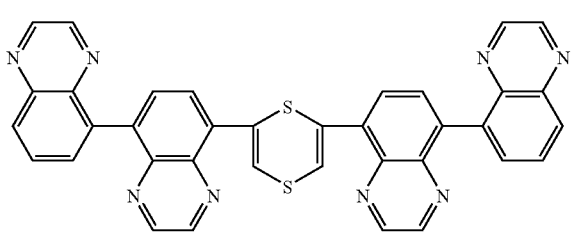
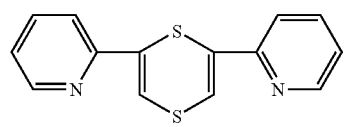
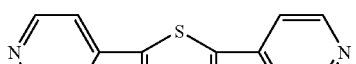
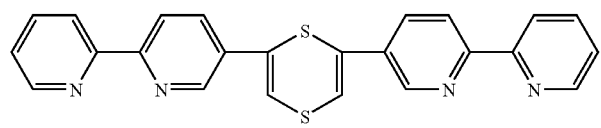
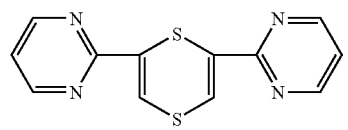
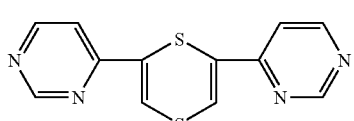
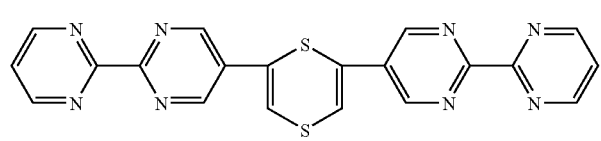
[Chemical Formula 21]
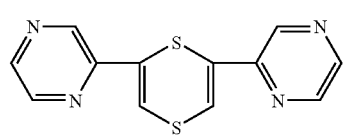
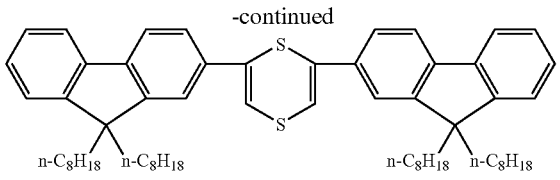
-continued
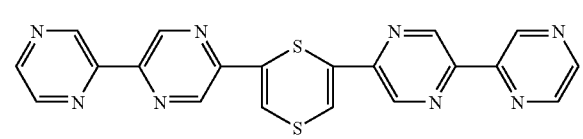
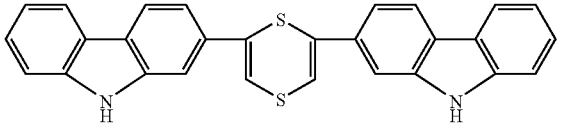
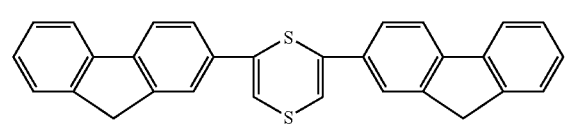

-continued

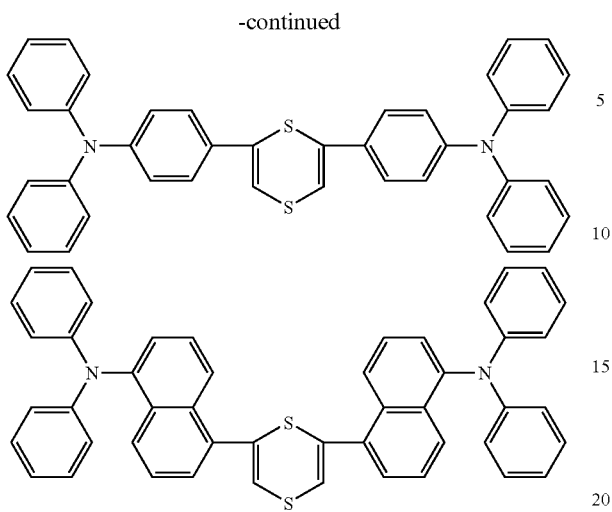

-continued

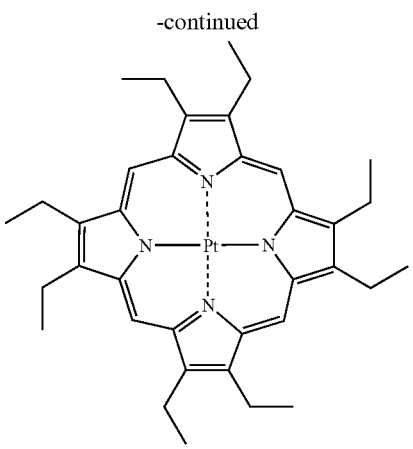

Of those compounds indicated above, use of the following compounds is preferred.

[Chemical Formula 22]

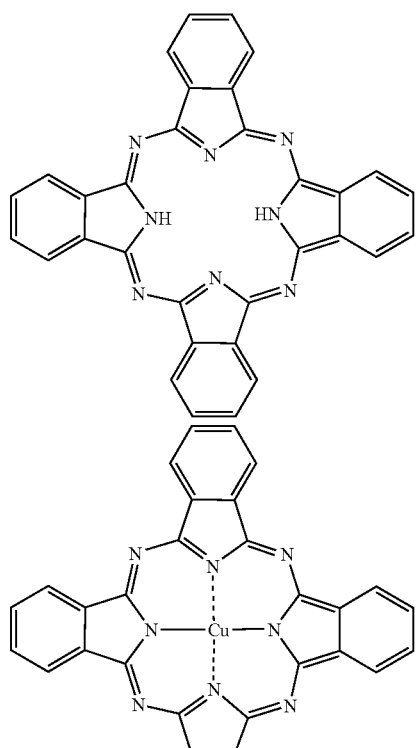

[Chemical Formula 23]

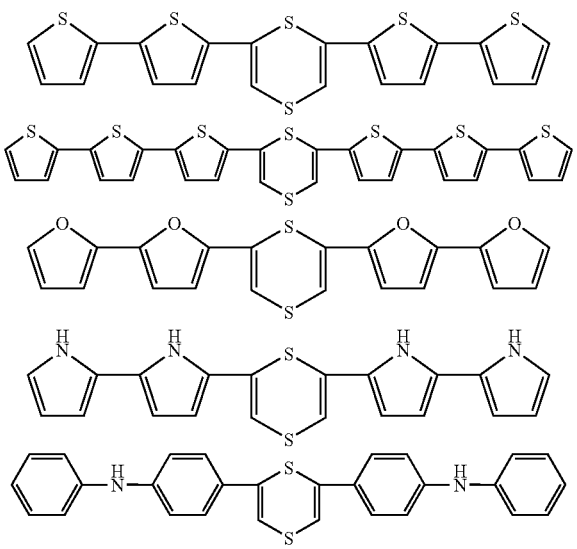

The method of synthesizing a compound containing a 1,4-dithiin ring is not limited to any specific one, and mention is made of methods described, for example, in document including Heterocycles, 1987, Vol. 26, pp. 939 to 942 and Heterocycles, 1987, Vol. 26, pp. 1793 to 1796. In the practice of the invention, it is preferred to use a preparation method composed of the following three steps.

[Chemical Formula 24]

First step

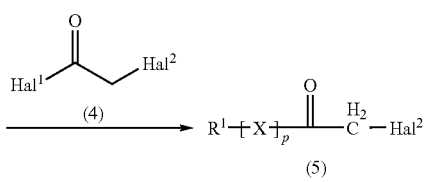

-continued

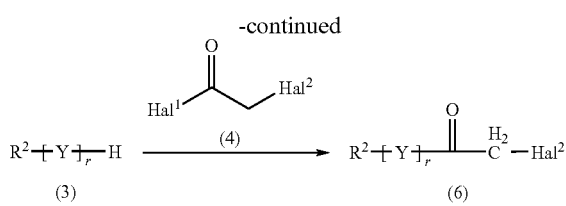

(wherein $R^1$, $R^2$, X, Y, p and r, respectively, have the same meanings as defined hereinbefore, and Hal represents a halogen atom).

[Chemical Formula 25]

Second step

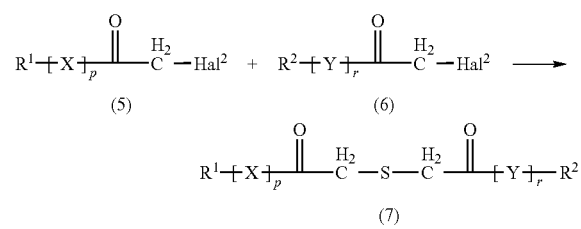

(wherein $R^1$, $R^2$, X, Y, p and r, respectively, have the same meanings as defined hereinbefore, and Hal represents a halogen atom).

[Chemical Formula 26]

Third step

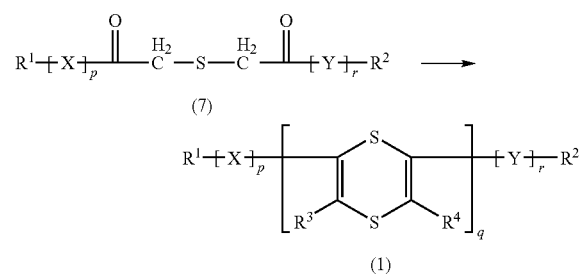

(wherein $R^1$, $R^2$, $R^3$, $R^4$, X, Y, p, q and r, respectively, have the same meanings as defined hereinbefore).

The first step is one wherein the starting compound represented by the formula (2) or (3) is acylated by use of an acid catalyst.

Specific examples of the compound represented by the formula (2) or (3) include thiophene, 2,2'-bithiophene (hereinafter abbreviated as BT), 2,2':5',2"-terthiophene, diphenylamine, N,N'-dipehnyl-1,4-phenylenediamine, furan, 2,2'-bifuran, 2,2':5',2"-terfuran, pyrrole, 2,2'-bipyrrole, 2,2':5',2"-terpyrrole, 1,2-di(2-thienyl)ethylene, 1,2-di(2-thienyl)acetylene, 1,2-di(2-furyl)ethylene, 1,2-di(2-furyl)acetylene, 2-furylthiophene, 5-furyl-2,2'-bithiophene, 2-phenylthiophene, 2-biphenylthiophene, 5-phenyl-2,2'-bithiophene, benzene, biphenyl, p-terphenyl, naphthalene, binaphthyl, anthracene, imidazole, biimidazole, oxazole, bioxazole, oxadiazole, bioxadiazole, quinoline, biquinoline, quinoxaline, biquinoxaline, pyridine, bipyridine, pyrimidine, bipyrimidine, pyrazine, bipyrazine, fluorene, carbazole, triphenylamine, meal-free phthalocyanine, copper-phthalocyanine, metal-free porphyrin, platinum-porphyrin derivatives and the like. Preferably, 2,2'-bithiophene, 2,2':5',2"-terthiophene, diphenylamine, 2,2'-bipyrrole and the like are mentioned.

The acrylating reagent is one represented by the formula (4) and specific examples include 2-chloroactyl chloride, 2-chloroacetyl fluoride, 2-chloroactyl bromide, 2-chloroacetyl iodide, 2-fluoroacetyl chloride, 2-bromoacetyl chloride, and 2-iodoacetyl chloride, of which 2-chloroacetyl chloride is preferred.

The amount of the acylating reagent is preferably in the range of 0.8 to 1.5 times by mole, more preferably 1.0 to 1.2 times by mole of the starting compound represented by the formula (2) or (3).

The acid catalyst preferably includes Lewis acid, and ethylaluminum dichloride and diethylaluminium chloride are more preferred.

The amount of the acid catalyst is preferably in the range of 0.1 to 5.0 times by mole, more preferably 1.0 to 1.2 times by mole of the starting compound represented by the formula (2) or (3).

The reaction solvent preferably includes an aprotic solvent such as dichloromethane, dichloroethane, chloroform, carbon tetrachloride, nitromethane, acetonitrile, diisopropyl ether, cyclohexane or the like, of which dichloromethane and dichloroethane are more preferred.

The amount of the reaction solvent should preferably range 1 to 200 times by weight, more preferably 5 to 30 times by weight, of the starting compound represented by the formula (2) or (3).

The reaction time generally ranges approximately −80 to 50° C., preferably −20 to 30° C.

It will be noted that how the reaction proceeds is detectable through a thin layer chromatography (hereinafter abbreviated as TLC) or liquid chromatography (hereinafter abbreviated as LC).

After completion of the reaction, purification is enabled by a liquid-liquid extraction operation, a washing operation, a solid-liquid extraction operation, a thermal filtration operation, a concentration operation and a drying operating. Although a subsequent step is allowed to proceed after completion of these simple operations alone, and a further improvement in purity is ensured if a recrystallization operation or silica gel column chromatography is carried out.

Through the operations set out hereinabove, an acyl compound represented by the formula (5) or (6) is obtained.

The second step is one wherein a sulfide represented by the formula (7) is obtained from the acyl compound of the formula (5) or (6) obtained in the first step.

The ratio between the acyl compound represented by the formula (5) and the acyl compound represented by the formula (6) is not specifically limited and should preferably be at 1:1, or the compounds should preferably be identical to each other.

For the sulfide reaction reagent, mention is made of lithium sulfide, sodium sulfide, potassium sulfide, cesium sulfide and the like, of which sodium sulfide is preferred.

The amount of the sulfide reaction preferably ranges 0.2 to 1.2 times by mole, more preferably 0.45 to 0.55 times by mole, of the total moles of the acyl compound represented by the formula (5) and the acyl compound represented by the formula (6), both used in the reaction.

The reaction solvent is not critical in type provided that it is able to dissolve part or all of the starting compounds and the alkali metal sulfide. Preferably, mention is made of mixed solvents of water-soluble organic solvents, such as acetone, 2-butanone, tetrahydrofuran, dioxane, nitromethane, acetonitrile, N,N-dimethylformamide, N,N-dimethylacetamide, N-methylpyrrolidone, 1,3-dimethylimidazolidinone, dimethylsulfoxide, methanol, ethanol, n-propanol, i-propanol, n-butanol, i-butanol, t-butanol, 2-methoxyethanol, 1,2-propyleneglycol, diethylene glycol diethyl ether and the like, and water.

The mixing ratio between the organic solvent and water is not critical, and is preferably such that the water content in the mixed solvent ranges 10 to 50 wt %.

The amount of the reaction solvent preferably ranges 1 to 200 times by weight, preferably 5 to 30 times by weight, of the total weight of the acyl compound represented by the formula (5) and the acyl compound represented by the formula (6), both used in the reaction.

The reaction temperature generally ranges approximately −20 to 100° C., preferably 0 to 60° C. The reaction proceeding is detectable by TLC or LC.

After completion of the reaction, purification is feasible by a liquid-liquid extraction operation, a washing operation, a concentration operation and a drying operation. Although a subsequent step is enabled after completion of these simple operations alone, a further improvement in purity is ensured when a recrystallization operation of silica gel column chromatography is carried out.

Through the above operations, the sulfide represented by the formula (7) is obtained.

The third step is one wherein a thiocarbonylizing reagent is acted on the sulfide of the formula (7) obtained in the second step to cyclize the sulfide thereby preparing a compound of the formula (1) having a 1,4-dithiin ring.

For the thiocarbonylizing reagent, mention is made of a Lawson reagent, sodium sulfide, hydrogen sulfide and the like, of which a Lawson reagent is preferred.

The amount of the thiocarbonylizing reagent is such that the sulfide represented by the formula (7) preferably ranges 0.3 to 5.0 times by mole, more preferably 0.8 to 1.5 times by mole, relative to the starting compound.

The reaction solvent is not critical in type and preferably includes dichloromethane, dichloroethane, chloroform, carbon tetrachloride, nitromethane, acetonitrile, diisopropyl ether, tetrahydrofuran, dioxane, toluene, xylene, N,N-dimethylformamide, N,N-dimethylacetamide, N-methylpyrrolidone, N,N'-dimethylimidazolidinone or dimethylsulfoxide, of which dichloroethane, dioxane and toluene are more preferred.

The amount of the reaction solvent preferably ranges 1 to 200 times by weight, more preferably 5 to 50 times by weight, relative to the sulfide represented by the formula (7).

The reaction temperature for the thiocarbonylization generally ranges approximately 0 to 120° C., preferably 10 to 80° C. The degree of proceeding of the thiocarbonylization reaction is detectable by TLC or LC.

After completion of the thiocarbonylization reaction, the cyclization reaction sequentially proceeds to form a 1,4-dithiin ring. For facilitating the cyclization reaction, the reaction temperature may be changed as suited therefor. The cyclization reaction temperature preferably ranges 0 to 120° C., more preferably 10 to 80° C. It will be noted that the degree of proceeding of the cyclization reaction is detectable by TLC or LC.

After completion of the cyclization reaction, it is possible to obtain an intended product of a satisfactory purity after having subjected to a concentration operation and a silica gel chromatography operation alone.

Through the operations stated hereinabove, there can be obtained a compound of the formula (1) having a 1,4-dithiin ring.

As set forth hereinbefore, when the compound of the formula (1) having a 1,4-dithiin ring, or a combination thereof further with a charge accepting dopant substance, is dissolved in or uniformly dispersed in a solvent, a charge transporting varnish can be prepared.

The charge accepting dopant substance should preferably have high charge accepting properties, and as to solubility, no limitation is placed on the type of substance in so far as to be dissolved in at least one type of solvent.

Specific examples of the electron accepting dopant substance include: inorganic strong acids such as hydrogen chloride, sulfuric acid, nitric acid, phosphoric acid and the like; Lewis acids such as aluminium (III) chloride ($AlCl_3$), titanium (IV) tetrachloride ($TiCl_4$), boron tribromide ($BBr_3$), boron trifluoride ether complex ($BF_3.OEt_2$), iron (III) chloride ($FeCl_3$), copper (II) chloride ($CuCl_2$), antimony (V) pentachloride ($SbCl_5$), arsenic (V) pentafluoride ($AsF_5$), phosphorus pentafluoride ($PF_5$), tri(4-bromophenyl)aluminium hexachloroantimonate (TBPAH) and the like; organic strong acids such as benzenesulfonic acid, tosyl acid, camphorsulfonic acid, hydroxybenzensulfonic acid, 5-sulfosalicylic acid, dodecylbenzenesulfonate, polystyrene sulfonate, 1,4-benzodioxanedisulfonic acid derivatives described in the specification of Japanese Patent Application No. 2003-181025, arylsulfonic acid derivatives described in the specification of Japanese Patent Application No. 2004-251774, dinonylnaphthalenesulfonic acid derivatives described in the specification of Japanese Patent Application No. 2003-320072 and the like; and organic or inorganic oxidizing agents such as 7,7,8,8-tetracyanoquinodimethane (TCNQ), 2,3-dichloro-5,6-dicyano-1,4-benzoquinone (DDQ), iodine and the like although not limited thereto.

Specific examples of the hole accepting substance include alkali metals (Li, Na, K, Cs), and metal complexes such as lithium quinolinolato (Liq), lithium acetylacetonate (Li(acac)) and the like although not limited to these.

For preferred charge accepting dopant substances, mention is made of electron accepting dopant substances of organic strong acids including 5-sulfosalicylic acid, dodecylbenzensulfonic acid, polystyrenesulfonic acid, 1,4-benzodioxanedisulfonic acid derivatives described in the specification of Japanese Patent Application No. 2003-181025, dinonylnaphthalenesulfonic acid derivatives described in the publication of Japanese Patent Application No. 2003-320072 and the like.

For the solvent used for the preparation of a charge transporting varnish, there can be used water; and organic solvents such as methanol, N,N-dimethylformamide, N,N-dimethylacetamide, N-methylpyrrolidone, N,N'-dimethylimidazolidinone, dimethylsulfoxide, chloroform, toluene and the like. For the reason stated hereinbefore, organic solvents are preferred, of which N,N-dimethylformamide, N,N-dimethylacetamide, N-methylpyrrolidone and N,N'-dimethylimidazolidinone are more preferred.

Aside from the above-indicated solvents, another type of solvent capable of imparting flatness to a film at the time of baking for the purposes of improvement of wettability to substrate, control of the surface tension of solvent, polarity control, boiling point control and the like may be mixed in an amount of 1 to 90 wt %, preferably 1 to 50 wt %, based on the total of the solvents used in the varnish.

Specific examples of such a solvent include butyl cellosolve, diethylene glycol diethyl ether, dipropylene glycol monomethyl ether, ethyl carbitol, diacetone alcohol, γ-butyrolactone, ethyl lactate, acetonitrile, ethanol, n-propanol, i-propanol, n-butanol, i-butanol, t-butanol, acetone, 2-butanone, carbon disulfide, nitromethane and the like although not limited thereto.

When the charge transporting varnish is coated onto a substrate and the solvent is evaporated, a charge transporting film can be formed on the substrate.

The coating method is not critical and includes a dipping method, a spin coating method, a transfer printing method, a roll coating method, a brushing method, an ink jet method, a spraying method and the like.

The solvent evaporation method is not critical and evaporation is feasible, for example, by use of a hot plate or oven in an appropriate atmosphere, i.e. in an inert gas such as nitrogen or the like, or in vacuum, thereby enabling one to obtain a uniformly film-formed face.

Within the confines of that the solvent can be evaporated, the baking temperature is not limited, and baking is preferably carried out at 40 to 250° C. In this case, the temperature may be changed by two or more stages for the purposes of developing more uniform film formation and permitting the reaction to proceed on the substrate.

The thickness of the charge transporting thin film obtained by the coating and evaporation operations is not critical. If the film is used as a charge injection layer in an organic EL element, the thickness preferably ranges 5 to 200 nm. For a measure of changing the film thickness, mention is made of a method wherein a solid concentration in the varnish is changed or a method wherein an amount of the solution on a substrate is changed upon coating.

The method of making an OLED element using a charge transporting varnish and the materials used according to the invention are stated hereinbelow and should not be construed as being limited thereto.

It is preferred that the electrode substrate used should beforehand be washed with a liquid such as a detergent, an alcohol, pure water or the like. For instance, an anode substrate should preferably be subjected to surface treatment such as ozone treatment, oxygen-plasma treatment or the like immediately before use. It should be noted that if the anode material is made mainly of an organic matter, the surface treatment may not be effected.

Where a hole transporting varnish is used in an OLED element, the following methods can be mentioned. The hole transporting varnish is coated onto an anode substrate and a hole transport thin film is formed on the electrode by the above-mentioned method. This is introduced into a vacuum deposition apparatus, followed by successively vacuum depositing a hole transport layer, a emission layer, an electron transport layer, an electron injection layer and a cathode metal thereby providing an OLED element. In order to control an emission region, a carrier block layer may be provided between arbitrary layers.

For the anode material, a transparent electrode is mentioned, typical of which is indium tin oxide (ITO) or indium zinc oxide (IZO), and should preferably be planarized. Alternatively, polythiophene derivatives and polyanilines having high charge transportability may also be used.

For material forming a hole transport layer, mention is made of triarylamines such as (triphenylamine)dimer derivatives (TPD), (α-naphthyldiphenylamine)dimer (α-NPD), [(triphenylamine)dimer], spiro dimer (spiro-TAD) and the like, star burst amines such as 4,4',4"-tris[3-methylphenyl (phenyl)amino]triphenylamine (m-MTDATA), 4,4',4"-tris[1-naphthyl(phenyl)amino]triphenylamine (1-TNATA) and the like, and oligothiophenes such as 5,5"-bis{4-[bis(4-methylphenyl)amino]phenyl}-2,2':5',2"-ter-thiophene (BMA-3T) and the like.

For a material forming an emission layer, mention is made of aluminium (III) tris(8-quinolinolate) ($Alq_3$), zinc (II) bis (8-quinolinolate) ($Znq_2$), aluminium (III) bis(2-methyl-8-quinolinolate)(p-phenylphenolate (BAlq), 4,4'-bis(2,2-diphenylbinyl)biphenyl (DPVBi) and the like. The emission layer may be formed by co-deposition of an electron transport material or a hole transport material and a light-emitting dopant.

For the electron transport material, $Alq_3$, BAlq, DPVBi, (2-(4-biphenyl)-5-(4-t-butylphenyl)-1,3,4-oxadiazole) (PBD), triazole derivatives (TAZ), bathocuproin (BCP), sylol derivatives and the like.

The light emitting dopant includes quinacridone, rubrene, coumarin 540, 4-(dicyanomethylene)-2-methyl-6-(p-dimethylaminostyryl)-4H-pyrane (DCM), iridium (III)tris(2-phenylpyridine)($Ir(ppy)_3$), europium (III)(1,10-phenanthrorine)-tris(4,4,4-trifluoro-1-(2-thienyl)-butan-1,3-dionate)(Eu $(TTA)_3$phen) or the like.

For a material forming the carrier block layer, mention is made of PBD, TAZ, BCP and the like.

For a material forming the electron injection layer, there are mentioned lithium oxide ($Li_2O$), magnesium oxide (MgO), alumina ($Al_2O_3$), lithium fluoride (LiF), magnesium fluoride ($MgF_2$), strontium fluoride ($SrF_2$), Liq, Li(acac), lithium acetate, lithium benzoate and the like.

The cathode material includes aluminium, magnesium-silver alloys, aluminium-lithium alloys, lithium, sodium, potassium, cesium or the like.

The method of making an OLED element using the charge transport varnish of the invention is not critical and the following methods may be mentioned.

An electron transporting varnish is coated onto a cathode substrate to from an electron transport thin film, and is subsequently introduced into a vacuum deposition apparatus, followed by forming an electron transport layer, an emission layer, a hole transport layer and a hole injection layer using such materials as indicated above, respectively, and subjecting an anode material to film formation such as by sputtering or the like to provide an OLED element.

The method of making a PLED element using the charge transporting varnish of the invention is not critical, and the following method is mentioned.

In the fabrication of the OLED element as set out hereinabove, a PLED element including a charge transport thin film formed of the charge transporting varnish of the invention can be made by forming a light-emitting, charge transport polymer layer in place of the vacuum deposition operations of the hole transport layer, emission layer, electron transport layer and electron injection layer.

More particularly, the hole transporting varnish is coated onto an anode substrate to from a hole transport thin film according to such a procedure as set forth hereinabove, over which a light-emitting transport polymer layer is formed, followed by vacuum deposition of a cathode electrode, thereby providing a PLED element.

Alternatively, the electron transporting varnish is coated onto a cathode substrate to form an electron transport thin film according to such a procedure as set out hereinabove, over which a light-emitting charge transport polymer layer is formed, followed by forming an anode electrode by a method such as sputtering, vacuum deposition, spin coating or the like, thereby providing a PLED element.

For the anode and cathode materials used, such substances as used for making an OLED element may be used, and similar cleaning and surface treatments may be carried out.

For the formation of the light-emitting charge transport polymer layer, mention is made of a method wherein a solvent is added to a light-emitting charge transport polymer material or a material obtained by adding a light-emitting dopant thereto for dissolution or uniform dispersion, followed by coating onto an electrode substrate on which a hole injection layer has been formed, followed by evaporation of the solvent to form a film.

The light-emitting charge transport polymer materials include polyfluorene derivatives such as poly(9,9-dialkylfluorene) (PDAF) and the like, polyphenylene vinylene derivatives such as poly(2-methoxy-5-)2'-ethylhexoxy)-1,4-phenylene vinylene) (MEH-PPV) and the like, polythiophene derivatives such as poly(3-alkylthiophene) (PAT) and the like, polyvinylcarbazole (PVCz), and the like.

Toluene, xylene, chloroform and the like can be mentioned as a solvent. For the dissolution or uniform dispersion, there are mentioned those methods of dissolution or uniform dispersion by agitation, thermal agitation, supersonic dispersion and the like methods.

The coating method is not critical and includes an ink jet method, a spraying method, a dipping method, a spin coating, a transfer printing method, a roll coating method, a brushing method and the like. It will be noted that coating should preferably be conducted in an inert gas such as nitrogen, argon or the like.

For the evaporation of solvent, there is mentioned a method of heating with an oven or hot plate in an inert gas or in vacuum.

EXAMPLES

Examples and Comparative Examples are shown to particularly illustrate the invention, and the following examples should not be construed as limiting the invention thereto.

Example 1

According to the following procedure, 2,6-bis(2,2'-bithiophenyl)-1,4-dithiin (hereinafter abbreviated as BBD) was prepared.

[Chemical Formula 27]

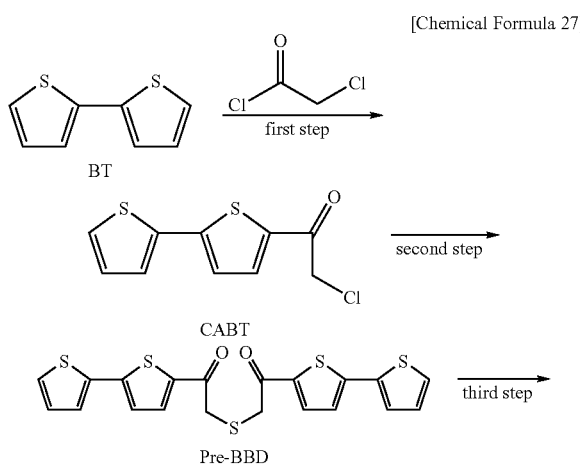

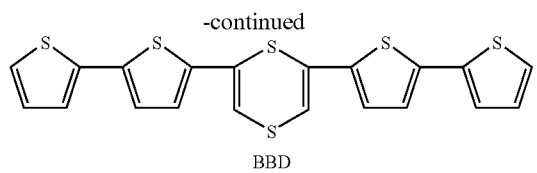

BBD

The first step is described below. 240 ml of dehydrated dichloromethane (made by Kanto Chem. Co. Inc.) was added to and dissolved in 12.00 g (72.18 mmols) of starting 2,2'-bithiophene (abbreviated as BT and made by Tokyo Kasei Kogyou Co., Ltd.) in an atmosphere of nitrogen and cooled down to 0° C., followed by dropping 82.70 ml (79.39 mmols) of an n-hexane solution of 0.96 M of dichloroethyl aluminium in 13 minutes. The reaction system was successively agitated at 0° C. for 150 minutes and then at 20° C. for two hours, followed by adding 250 ml of chloroform to the reaction system and pouring the resulting solution into a violently agitated suspension of 500 ml of saturated sodium hydrogen carbonate and 250 ml of chloroform. After separation, the resulting aqueous phase was extracted with 100 ml of chloroform twice, and the combined organic phase was washed with 500 ml of pure water once, dried with Glauber's salt and concentrated to dryness under reduced pressure to obtain 16.95 g (69.82 mmols, with a yield of 97%) of 4-chloroacetyl-2,2'-bithiophene (hereinafter abbreviated as CABT).

The second step is described below. A solution was obtained by adding 106 ml of acetone (made by Junsei Chemical Co., Ltd.) to 5.32 g (21.92 mmols) of CABT obtained in a manner as stated hereinabove, in which a solution obtained by adding 53 ml of pure water to 2.632 g (10.96 mmols) of sodium sulfide nonahydrate was dropped in 15 minutes. The reaction system was sequentially agitated at 20° C. for three hours and then at 50° C. for 30 minutes and was allowed to cool down to room temperature, followed by concentration under reduced pressure and removal of the acetone by distillation. The resulting suspension was extracted with 300 ml of chloroform, and was successively washed with 100 ml of a saturated sodium hydrogen carbonate aqueous solution once and then with 100 ml of pure water once and dried with Glauber's salt, followed by concentration to dryness under reduced pressure to obtain 4.68 g (10.48 mmols, with a yield of 96%) of a 2,6-bis(2,2'-bithiophenyl)-1,4-dithiin precursor (abbreviated as pre-BBD).

The third step is now described below. 2.172 g (5.370 mmols) of a Lawson reagent (made by Tokyo Chemical Co., Ltd.) and 60 ml of dehydrated dichloroethane (Junsei Chem. Co., Ltd., dried with molecular sieves 4A) were successively added to 1.999 g (4.475 mmols) of the pre-BBD obtained as stated above, followed by agitation at a bath temperature of 65° C. (temperature raised up to an inner temperature of 61° C.) for 40 minutes. After allowing to cool down to room temperature, the solution was concentrated to dryness under reduced pressure and, after azeotropic boiling with toluene once, 2.5 g of silica gel was added to the resulting residue, followed by purification with silica gel chromatography (50 g of silica gel, hexane: toluene=2:1→chloroform) to obtain 1.012 g (2.276 mmols, with a yield of 51%) of BBD.

1.064 g (1.124 mmols) of an electron accepting dopant substance BDSO-3 obtained by a method set out in the specification of Japanese Patent Application No. 2003-181025 and 70 g of dimethylacetamide (DMAc) were successively added, in air, to 1.000 g (2.249 mmols) of BBD obtained above, and heated to 60° C. under agitation for dissolution, followed by allowing to cool down to room temperature to prepare a varnish. The thus obtained varnish was a reddish orange, transparent solution having a viscosity of 1.6 mPa·s.

The resulting varnish was coated onto an ITO glass substrate that had been subjected to ozone cleaning for 40 minutes by a spin coating method and baked with a hot plate in air to obtain a thin film. The ionization potentials (hereinafter abbreviated as $I_p$) for different baking conditions are shown in Table 1.

According to a similar procedure, the varnish was used to form a hole transport thin film on the ITO glass substrate, followed by introduction into a vacuum deposition apparatus for successive vacuum deposition of α-NPD, $Alq_3$, LiF and Al. The film thicknesses were, respectively, at 40 nm, 60 nm, 0.5 nm and 100 nm, and the deposition operations were, respectively, carried out when the pressure was reduced to $8 \times 10^{-4}$ Pa or below. The deposition rate was at 0.3 to 0.4 nm/second except for LiF and at 0.01 to 0.03 nm/second for LiF. The moving operation between the deposition operations was effected in vacuum. The characteristic properties of the resulting OLED are shown in Table 2.

Example 2

70 g of DMAc was added to 1.000 g (2.249 mmols) of BBD obtained by the method set out in Example 1 and 1.064 g (1.124 mmols) of the electron accepting dopant substance BDSO-3 obtained by the method set out in the specification of Japanese Patent Application No. 2003-181025 and heated to 60° C. for dissolution under agitation, followed by allowing to cool down to room temperature thereby preparing a varnish. The thus obtained varnish was a reddish orange, transparent solution, and it was found that no deposition of solid matter was observed when stored at −20° C. for a week.

[Chemical Formula 28]

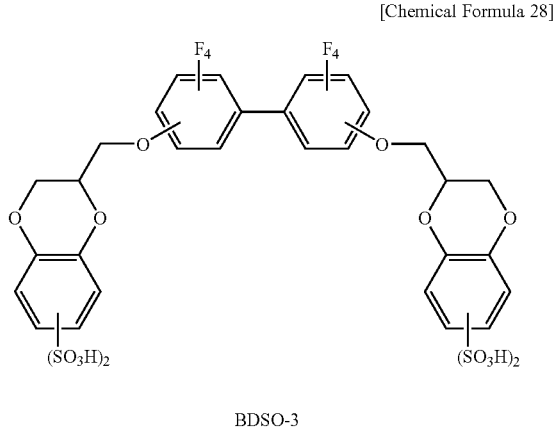

BDSO-3

Example 3

2.02 g of DMAC was added to 45.5 mg (0.102 mmols) of BBD obtained by the method set out in Example 1 and 48.4 mg (0.0511 mmols) of the electron accepting dopant substance BDSO-3 obtained by the method set forth in the specification of Japanese Patent Application No. 2003-181025 and heated to 50° C. for dissolution under agitation, to which 1.01 g of cyclohexanol was added and agitated, followed by allowing to cool down to room temperature, thereby preparing a varnish. The resulting varnish was a reddish orange, transparent solution, and it wad found that no precipitation of solid matter was observed when stored at −20° C. for a week.

Example 4

2.02 g of DMAc was added to 30.0 mg (0.0675 mmols) of BBD obtained by the method set out in Example 1 and 63.9 mg (0.0675 mmols) of the electron accepting dopant substance BDSO-3 obtained by the method set forth in the specification of Japanese Patent Application No. 2003-181025 and heated to 50° C. for dissolution under agitation, to which 1.01 g of cyclohexanol was added and agitated, followed by allowing to cool down to room temperature, thereby preparing a varnish. The resulting varnish was a reddish orange, transparent solution, and it was found that no precipitation of solid matter was observed when stored at −20° C. for a week.

Example 5

2.02 g of DMAC was added to 17.9 mg (0.0403 mmols) of BBD obtained by the method set out in Example 1 and 76.0 mg 0.5 (0.0803 mmols) of the electron accepting dopant substance BDSO-3 obtained by the method set forth in the specification of Japanese Patent Application No. 2003-181025 and heated to 50° C. for dissolution under agitation, to which 1.01 g of cyclohexanol was added and agitated, followed by allowing to cool down to room temperature, thereby preparing a varnish. The resulting varnish was a reddish orange, transparent solution, and it was found that no precipitation of solid matter was observed when stored at −20° C. for a week.

Example 6

The varnish obtained by the method set out in Example 2 was coated onto an ITO glass substrate, having subjected to ozone cleaning for 40 minutes, according to a spin coating method and baked in air by means of a hot plate to obtain a thin film. The ionization potential (hereinafter abbreviated as $I_p$) of the thin film relative to sintering conditions is indicated in Table 1.

According to a similar procedure, a hole transport thin film was formed on the ITO glass substrate by use of the varnish and introduced into a vacuum deposition apparatus, followed by successive vacuum deposition of α-NPD, $Alq_3$, LiF and Al. The film thicknesses were, respectively, at 40 nm, 60 nm, 0.5 nm and 100 nm, and the respective deposition operations were carried out at a pressure of $8 \times 10^{-4}$ Pa or below. The deposition rate was at 0.35 to 0.40 nm/second except for LiF and was at 0.01 to 0.03 nm/second for LiF. The moving operation between individual deposition operations was effected in vacuum. When a voltage was applied to the resulting OLED element, light was emitted uniformly from an entire light-emitting face with no defect being observed. The characteristic properties of the resulting OLED element are shown in Table 2.

Example 7

Such a film formation operation on an ITO glass substrate using the varnish obtained by the procedure set out in Example 3 was effected according to the method set forth in Example 6 to provide an OLED element. The thus obtained OLED element was applied with a voltage, uniform light emission throughout the light-emitting face was observed with no defect involved therein. The photograph of the light emitting face of the OLED element is shown in FIG. 1. The characteristics of the resulting $I_p$ and OLED of the thin film are, respectively, shown in Tables 1 and 2.

Example 8

Film formation operation on an ITO glass substrate using the varnish obtained by the procedure set out in Example 4 was effected according to the method set forth in Example 6 to provide an OLED element. The thus obtained OLED element was applied with a voltage, uniform light emission throughout the light-emitting face was observed with no defect involved therein. The characteristics of the resulting $I_p$ and OLED of the thin film are, respectively, shown in Tables 1 and 2.

Example 9

Film formation operation on an ITO glass substrate using the varnish obtained by the procedure set out in Example 5 was effected according to the method set forth in Example 6 to provide an OLED element. The thus obtained OLED element was applied with a voltage, uniform light emission throughout the light-emitting face was observed with no defect involved therein. The characteristics of the resulting $I_p$ and OLED characteristics of the thin film are, respectively, shown in Tables 1 and 2.

Comparative Example 1

According to the method described in Non-patent Document 10, a thiophene pentamer was synthesized. The resulting thiophene pentamer was insoluble in DMAC, and the resulting solution was left as being colorless, transparent.

[Chemical Formula 29]

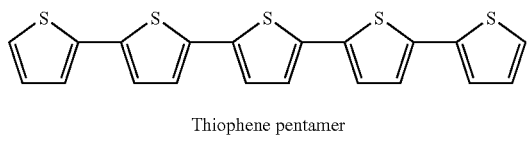

Thiophene pentamer

Comparative Example 2

An ITO glass substrate under such conditions as in Example 6 was introduced into a vacuum deposition apparatus, followed by successive vacuum deposition of α-NPD, Alq$_3$, LiF and Al under the same conditions as used in the procedure of Example 1 but without forming a hole injection layer. $I_p$ of the ITO glass substrate used is indicated in Table 1, and the characteristics of the resulting OLED element are shown in Table 2. It will be seen that the OLED element characteristics including current density, luminance and current efficiency are inferior to those of Examples 6 to 8 at the respective voltages of 5V and 7V.

Comparative Example 3

A polyethylenedioxythiophene-polystyrenesulfonic acid aqueous solution was spin coated onto an ITO glass substrate of such conditions as used in Example 6 and baked to provide a uniform thin film. The baking conditions and $I_p$ of the resulting thin film are shown in Table 1.

A hole transport thin film was formed on an ITO glass substrate according to a similar method to make an OLED element under such conditions as with the method set out in Example 1. The characteristic properties of the thus obtained OLED element are shown in Table 2. It will be seen that the OLED element characteristics including the luminance and current efficiency at the respective voltages of 5V and 7V are inferior to those of Examples 6 to 8.

Comparative Example 4

Figure 2:
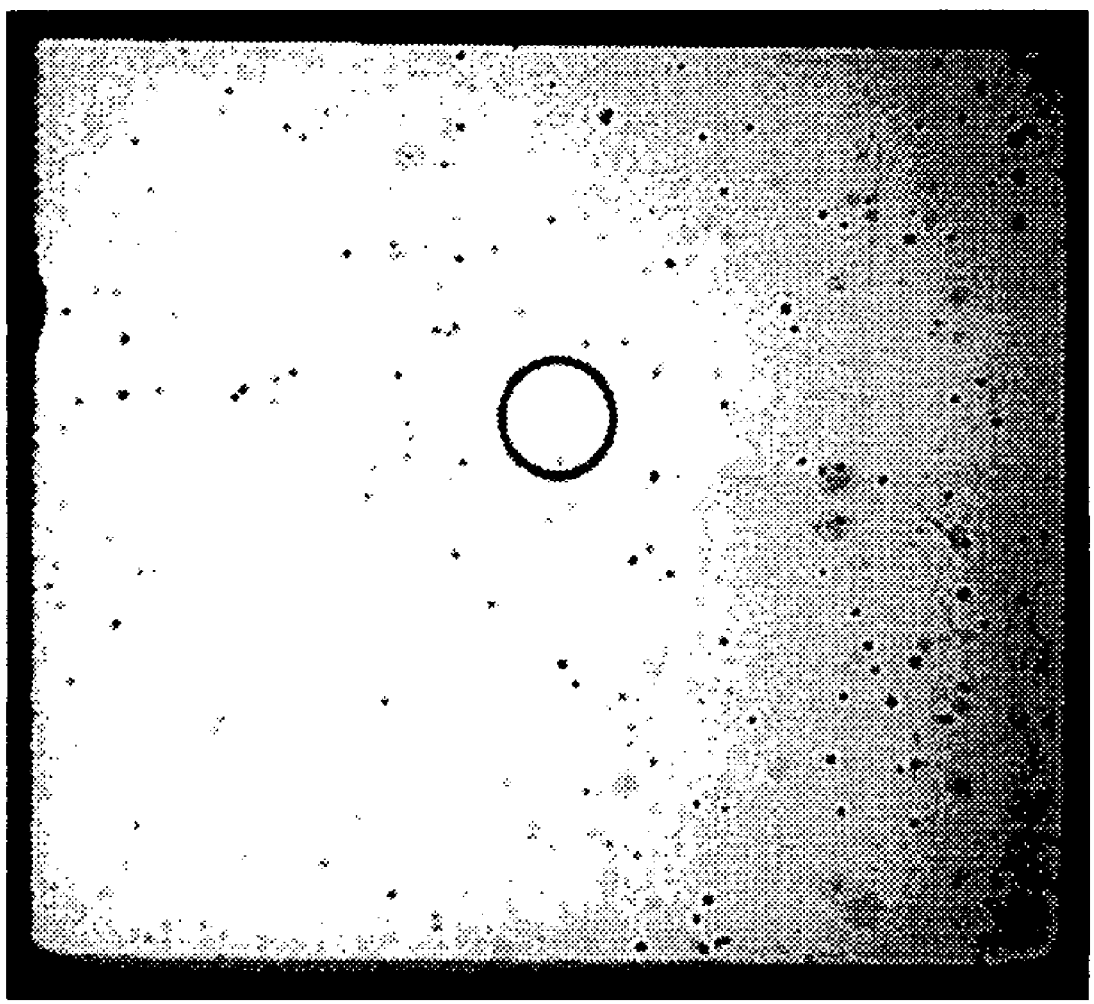
FIG. 2 is a view showing a photograph of a luminous face of an OLED element obtained in Comparative Example 4.

Using CuPC (film thickness of 25 nm and deposition rage of 0.35 to 0.40 nm/second) as a hole injection layer, α-NPD, Alq$_3$, LiF and Al were successively deposited under the same conditions as used in the method set out in Example 1. The photograph of the light-emitting face of the resulting OLED element is shown in FIG. 2.

In the foregoing examples and comparative examples, the viscosity was measured by use of an E-type viscometer ELD-50, made by Tokyo Keiki. The film thickness was measured by use of a surface profiler DEKTAK3ST, made by ULVAC. The ammeter used was Digital Multimeter 7555, made by Yokogawa Electric Corp., a voltage generator was DC voltage current source R6145, made by Advantest, and a luminance meter was luminance meter BM-8, made by Topcon Corporation. The ionization potential was measured by use of photoelectron spectrometer AC-2, made by Riken Keiki Co., Ltd.

TABLE 1

|  | Baking Conditions | $I_p$ [eV] |
|---|---|---|
| Example 6 (1) | 180° C., 30 minutes | 5.67 |
| Example 6 (2) | 220° C., 15 minutes | 5.69 |
| Example 7 | 180° C., 30 minutes | 5.76 |
| Example 8 | 180° C., 30 minutes | 5.82 |
| Example 9 | 180° C., 30 minutes | 6.01 |
| Comparative Example 2 | — | 5.10 |
| Comparative Example 3 | 120° C., 1 hour | 5.61 |

TABLE 2

|  | Voltage [V] | Current Density [mA/cm$^2$] | Luminance [cd/m$^2$] | Current Efficiency [cd/A] | Emission Commencing Voltage [V] | Maximum Luminance [cd/m$^2$] |
|---|---|---|---|---|---|---|
| Example 6 (1) | 5.0 | 0.17 | 9.4 | 5.6 | 2.5 | 23650 |
|  | 7.0 | 2.3 | 161 | 6.9 |  |  |
| Example 6 (1) | 5.0 | 0.81 | 40 | 5.0 | 2.5 | 26210 |
|  | 7.0 | 8.2 | 507 | 6.2 |  |  |
| Example 7 | 5.0 | 4.3 | 133 | 3.1 | 2.5 | 20530 |
|  | 7.0 | 24 | 893 | 3.8 |  |  |
| Example 8 | 5.0 | 1.4 | 45 | 3.2 | 2.5 | 14760 |
|  | 7.0 | 7.6 | 305 | 4.90 |  |  |
| Example 9 | 5.0 | 0.11 | 3.2 | 3.0 | 2.5 | 5012 |
|  | 7.0 | 0.45 | 17 | 3.7 |  |  |

TABLE 2-continued

| | Voltage [V] | Current Density [mA/cm$^2$] | Luminance [cd/m$^2$] | Current Efficiency [cd/A] | Emission Commencing Voltage [V] | Maximum Luminance [cd/m$^2$] |
|---|---|---|---|---|---|---|
| Comparative Example 2 | 5.0 | 0.14 | 0.02 | 0.01 | 4.50 | 10640 |
| | 7.0 | 0.37 | 1.2 | 0.31 | | |
| Comparative Example 3 | 5.0 | 0.22 | 3.1 | 1.4 | 2.75 | 5610 |
| | 7.0 | 11 | 253 | 2.9 | | |

The invention claimed is:

1. A charge transport organic material comprising an electron accepting dopant substance or a hole accepting dopant substance, and a compound of the general formula (1) having a 1,4-dithiin ring

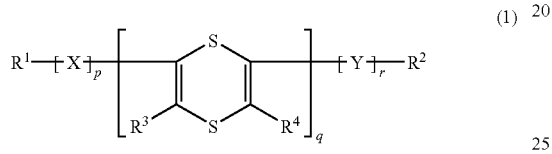

wherein $R^1$, $R^2$, $R^3$ and $R^4$ independently represent hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group, an organooxy group, an organoamino group, an organosilyl group, an organothio group, an acyl group or a sulfone group, X and Y independently represent at least one member of substituted or unsubstituted, divalent conjugated units selected from aniline, thiophene, furan, pyrrole, ethynylene, vinylene, phenylene, naphthalene, anthracene, imidazole, oxazole, oxadiazole, quinoline, quinoxaline, pyridine, pyrimidine, pyrazine, phenylenevinylene, fluorene, carbazole, triarylamines, metal or metal-free phthalocyanine, and metal or metal-free porphyrin, two sulfur atoms contained in the dithiin ring may independently be in the form of an SO group or an SO$_2$ group, and p and r independently represent 0 or an integer of 1 or over, q represents an integer of 1 or over, provided that p+q+r≦20 is satisfied.

2. The charge transport organic material according to claim 1, wherein p, q and r in the general formula (1) satisfies that 3≦p+q+r≦10.

3. A charge transport varnish comprising a charge transport organic material of claim 1 and a solvent.

4. A charge transport thin film prepared by use of the charge transport varnish defined in claim 3.

5. An organic electroluminescent element comprising the charge transport thin film defined in claim 4.

6. A method for preparing a compound having a 4-dithiin ring and represented by the formula (1) indicated hereinbelow, comprising:

the first step of reacting, in the presence of an acid catalyst, a compound of the formula (2)

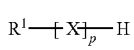

$R^1$ hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group or an organooxy group, X represents at least one member of substituted or unsubstituted, divalent conjugated units selected from aniline, thiophene, furan, pyrrole, ethynylene, vinylene, phenylene, naphthalene, anthracene, imidazole, oxazole, oxadiazole, quinoline, quinoxaline, pyridine, pyrimidine, pyrazine, phenylenevinylene, fluorene, carbazole, triarylamines, metal or metal-free phthalocyanine, and metal or metal-free porphyrin, and p is an 0 or an integer of 1 or over, or a compound of the formula (3)

wherein $R^2$ hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group or an organooxy group, Y represents at least one member of substituted or unsubstituted, divalent conjugated units selected from aniline, thiophene, furan, pyrrole, ethynylene, vinylene, phenylene, naphthalene, anthracene, imidazole, oxazole, oxadiazole, quinoline, quinoxaline, pyridine, pyrimidine, pyrazine, phenylenevinylene, fluorene, carbazole, triarylamines, metal or metal-free phthalocyanine, and metal or metal-free polyphyrin, and r is an 0 or an integer of 1 or over, and an acid halide represented by the formula (4)

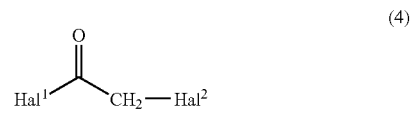

wherein Hal represents a halogen atom, thereby preparing an acyl compound represented by the formula (5)

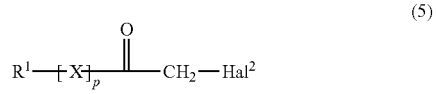

wherein R¹, X, p and Hal, respectively, have the same meanings as defined above, or the formula (6)

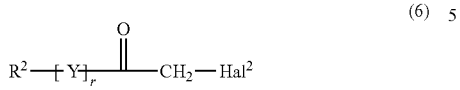
(6)

wherein R², Y, r and Hal, respectively, have the same meanings as defined above;

the second step of subsequently reacting the acyl compound represented by the formula (5), the acyl compound represented by the formula (6) and an alkali metal sulfide to prepare a sulfide represented by the formula (7)

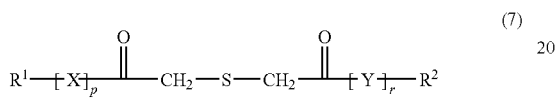
(7)

wherein R¹, R², X, Y, p and r, respectively, have the same meanings as defined above; and the third step of acting a thiocarbonyl reagent on the sulfide represented by the formula (7) for ring-closure, thereby preparing the compound of the formula (1) having a 1,4-dithiin ring

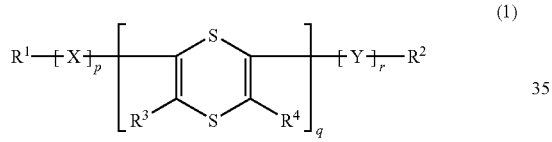
(1)

wherein R¹, R², X, Y, p and r, respectively, have the same meanings as defined above, R³ and R⁴ independently represent hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group, an organooxy group, an organoamino group, an organosilyl group, an organothio group, an acyl group or a sulfone group, two sulfur atoms contained in the dithiin ring may independently be in the form of an SO group or an SO₂ group, and q is an integer of 1 or over provided that p+q+r≦20 is satisfied.

7. The method according to claim 6, further comprising preparing the acyl compound of the formula (5) or (6) indicated hereinbelow, comprising:

reacting, in the presence of an acid catalyst, a compound of the formula (2)

(2)

wherein R¹ represents hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group or an organooxy group, X represents at least one member of substituted or unsubstituted, divalent conjugated units selected from aniline, thiophene, furan, pyrrole, ethynylene, vinylene, phenylene, naphthalene, anthracene, imidazole, oxazole, oxadiazole, quinoline, quinoxaline, pyridine, pyrimidine, pyrazine, phenylenevinylene, fluorene, carbazole, triarylamine, metal or metal-free phthalocyanine, and metal or metal-free porphyrin, and p is 0 or an integer of 1 or over, or the formula (3)

(3)

wherein R² represents hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group or an organooxy group, Y represents at least one member of substituted or unsubstituted, divalent conjugated units selected from aniline, thiophene, furan, pyrrole, ethynylene, vinylene, phenylene, naphthalene, anthracene, imidazole, oxazole, oxadiazole, quinoline, quinoxaline, pyridine, pyrimidine, pyrazine, phenylenevinylene, fluorene, carbazole, triarylamine, metal or metal-free phthalocyanine, and metal or metal-free porphyrin, and r is 0 or an integer of 1 or over, and an acid halide of the formula (4)

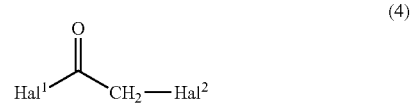
(4)

wherein Hal represents a halogen atom, thereby preparing the acyl compound of either the formula (5)

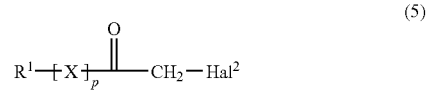
(5)

wherein R¹, X, p and Hal, respectively, have the same meanings as defined above, or the formula (6)

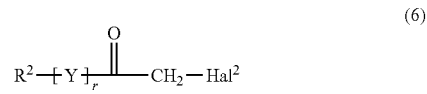
(6)

wherein R², X, r and Hal, respectively, have the same meanings as defined above.

8. The method for preparing an acyl compound according to claim 7, wherein said acid catalyst is made of ethyl aluminium dichloride or diethyl aluminium chloride.

9. A method for preparing a sulfide represented by the formula (7) indicated hereinbelow, comprising reacting the acyl compound represented by the formula (5), the acyl compound represented by the formula (6), both obtained in claim 7 or 8, and an alkali metal sulfide

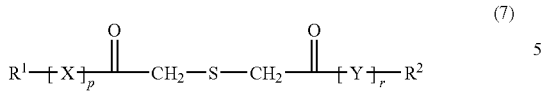  (7)

wherein $R^1$, $R^2$, X, Y, p and r, respectively, have the same meanings as defined above.

10. A method for preparing a compound having a 1,4-dithiin ring and represented by the formula (1) indicated hereinbelow, comprising reacting a thiocarbonylizing reagent on the sulfide obtained in claim 9 and represented by the formula (7)

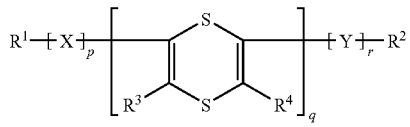  (1)

wherein $R^1$, $R^2$, X, Y, p and r, respectively, have the same meanings as defined above, and $R^3$ and $R^4$ independently represent hydrogen, a hydroxyl group, a halogen group, an amino group, a silanol group, a thiol group, a carboxyl group, a sulfonic acid group, a phosphoric acid group, a phosphoester group, an ester group, a thioester group, an amido group, a nitro group, a monovalent hydrocarbon group, an organooxy group, an organoamino group, an organosilyl group, an organothio group, an acyl group or a sulfone group, two sulfur atoms contained in the dithiin ring may independently be in the form of an SO group or an $SO_2$ group, and q is an integer of 1 or over provided that $p+q+r \leqq 20$ is satisfied.

11. The charge transport organic material according to claim 1, comprising 2,6-bis(2,2'-bithiopheny1)-1,4-dithiin.

12. A charge transport varnish comprising a charge transport organic material of claim 11 and a solvent.

13. A charge transport thin film prepared by use of the charge transport varnish defined in claim 12.

14. An organic electroluminescent element comprising the charge transport thin film defined in claim 13.

* * * * *